(12) United States Patent
Marshall

(10) Patent No.: US 8,759,309 B2
(45) Date of Patent: Jun. 24, 2014

(54) POLYNUCLEOTIDES THAT STIMULATE NEUTROPHILS

(75) Inventor: William E. Marshall, Naples, FL (US)

(73) Assignee: Immunom Technologies, Inc., Naples, FL (US)

( * ) Notice: Subject to any disclaimer, the term of this patent is extended or adjusted under 35 U.S.C. 154(b) by 77 days.

(21) Appl. No.: 13/031,863

(22) Filed: Feb. 22, 2011

(65) Prior Publication Data

US 2011/0268763 A1 Nov. 3, 2011

Related U.S. Application Data

(60) Provisional application No. 61/314,368, filed on Mar. 16, 2010.

(51) Int. Cl.
*C12N 15/11* (2006.01)

(52) U.S. Cl.
USPC ....................................... 514/44 A

(58) Field of Classification Search
USPC ....................................... 514/44 A
See application file for complete search history.

(56) References Cited

U.S. PATENT DOCUMENTS

| | | | |
|---|---|---|---|
| 6,232,120 | B1 | 5/2001 | Dropulic et al. |
| 2003/0186911 | A1 | 10/2003 | Goodchild et al. |
| 2003/0191078 | A1* | 10/2003 | Goodchild et al. ............ 514/44 |
| 2004/0162253 | A1* | 8/2004 | Vaillant et al. ................ 514/44 |
| 2005/0130921 | A1 | 6/2005 | Waldor et al. |
| 2006/0147465 | A1 | 7/2006 | Marshall |
| 2006/0204435 | A1* | 9/2006 | Stuart ......................... 424/1.49 |

OTHER PUBLICATIONS

Immunom Technologies, Inc. et al., PCT/US2011/025682, Notification of Transmittal of the International Search Report and the Written Opinion of the International Searching Authority or the Declaration, mailed Nov. 15, 2011, 7 pages.

* cited by examiner

*Primary Examiner* — Brian Whiteman
(74) *Attorney, Agent, or Firm* — McKee, Voorhees & Sease, P.L.C.

(57) ABSTRACT

The polynucleotides of the present invention are complementary to the Initiation Sites of microbes. Invading organisms, sensing the pH and nutrient deprivation of a physiologic environment quickly release these nucleotides triggering rapid growth and mutation—attributes to successfully establishing a nidus of infection. They also stimulate neutrophil functions. Accordingly, the nucleotides, compositions and methods of the present invention may be used to enhance, restore or stimulate an immune response or system of an animal, e.g. to prevent an infection caused by a microorganism, ameliorate an infection caused by a microorganism, or kill an invading microorganism that causes infection or re-establish balance to an immune system. In particular, the polynucleotides, compositions and methods of the present invention may be used to treat or prevent bacterial infections and auto-immune diseases in a mammal in need thereof.

15 Claims, No Drawings

SEQUENCE LISTING

<160> NUMBER OF SEQ ID NOS: 30

<210> SEQ ID NO 1
<211> LENGTH: 9
<212> TYPE: DNA
<213> ORGANISM: Artificial Sequence
<220> FEATURE:
<223> OTHER INFORMATION: bacterial consensus sequence

<400> SEQUENCE: 1 ttatccaca                                                                 9

<210> SEQ ID NO 2
<211> LENGTH: 9
<212> TYPE: DNA
<213> ORGANISM: Artificial Sequence
<220> FEATURE:
<223> OTHER INFORMATION: bacterial consensus sequence

<400> SEQUENCE: 2 tttggataa                                                                 9

<210> SEQ ID NO 3
<211> LENGTH: 10
<212> TYPE: DNA
<213> ORGANISM: Artificial Sequence
<220> FEATURE:
<223> OTHER INFORMATION: bacterial consensus sequence

<400> SEQUENCE: 3
ggttatacac                                                               10

<210> SEQ ID NO 4
<211> LENGTH: 9
<212> TYPE: DNA
<213> ORGANISM: Artificial Sequence
<220> FEATURE:
<223> OTHER INFORMATION: bacterial consensus sequence

<400> SEQUENCE: 4 tgtggataa                                                                 9

<210> SEQ ID NO 5
<211> LENGTH: 9
<212> TYPE: DNA
<213> ORGANISM: Artificial Sequence
<220> FEATURE:
<223> OTHER INFORMATION: bacterial consensus sequence
<220> FEATURE:
<221> NAME/KEY: misc_feature
<222> LOCATION: (5)..(5)
<223> OTHER INFORMATION: n is a, c, g, or t

<400> SEQUENCE: 5 ttatncaca                                                                 9

<210> SEQ ID NO 6
<211> LENGTH: 9
<212> TYPE: DNA
<213> ORGANISM: Artificial Sequence
<220> FEATURE:
<223> OTHER INFORMATION: bacterial consensus sequence

<400> SEQUENCE: 6 aataggtgt                                                                 9

```
<210> SEQ ID NO 7
<211> LENGTH: 9
<212> TYPE: DNA
<213> ORGANISM: Artificial Sequence
<220> FEATURE:
<223> OTHER INFORMATION: bacterial consensus sequence

<400> SEQUENCE: 7 aaacctatt                                                               9

<210> SEQ ID NO 8
<211> LENGTH: 11
<212> TYPE: DNA
<213> ORGANISM: Artificial Sequence
<220> FEATURE:
<223> OTHER INFORMATION: bacterial consensus sequence

<400> SEQUENCE: 8
ccaatatggt g                                                           11

<210> SEQ ID NO 9
<211> LENGTH: 9
<212> TYPE: DNA
<213> ORGANISM: Artificial Sequence
<220> FEATURE:
<223> OTHER INFORMATION: bacterial consensus sequence

<400> SEQUENCE: 9 acacctatt                                                               9

<210> SEQ ID NO 10
<211> LENGTH: 9
<212> TYPE: DNA
<213> ORGANISM: Artificial Sequence
<220> FEATURE:
<223> OTHER INFORMATION: bacterial consensus sequence
<220> FEATURE:
<221> NAME/KEY: misc_feature
<222> LOCATION: (5)..(5)
<223> OTHER INFORMATION: n is a, c, g, or t

<400> SEQUENCE: 10 aatangtgt                                                               9

<210> SEQ ID NO 11
<211> LENGTH: 9
<212> TYPE: RNA
<213> ORGANISM: Artificial Sequence
<220> FEATURE:
<223> OTHER INFORMATION: bacterial consensus sequence

<400> SEQUENCE: 11 aauaggugu                                                               9

<210> SEQ ID NO 12
<211> LENGTH: 9
<212> TYPE: DNA
<213> ORGANISM: Artificial Sequence
<220> FEATURE:
<223> OTHER INFORMATION: bacterial consensus sequence

<400> SEQUENCE: 12 ttatccaca                                                               9

<210> SEQ ID NO 13
<211> LENGTH: 9
<212> TYPE: RNA
```

```
<213> ORGANISM: Artificial Sequence
<220> FEATURE:
<223> OTHER INFORMATION: bacterial consensus sequence

<400> SEQUENCE: 13 uuauccaca                                                                 9

<210> SEQ ID NO 14
<211> LENGTH: 9
<212> TYPE: DNA
<213> ORGANISM: Artificial Sequence
<220> FEATURE:
<223> OTHER INFORMATION: bacterial consensus sequence

<400> SEQUENCE: 14 aataggtgt                                                                 9

<210> SEQ ID NO 15
<211> LENGTH: 9
<212> TYPE: RNA
<213> ORGANISM: Artificial Sequence
<220> FEATURE:
<223> OTHER INFORMATION: bacterial consensus sequence

<400> SEQUENCE: 15 aaaccuauu                                                                 9

<210> SEQ ID NO 16
<211> LENGTH: 9
<212> TYPE: DNA
<213> ORGANISM: Artificial Sequence
<220> FEATURE:
<223> OTHER INFORMATION: bacterial consensus sequence

<400> SEQUENCE: 16 tttggataa                                                                 9

<210> SEQ ID NO 17
<211> LENGTH: 9
<212> TYPE: RNA
<213> ORGANISM: Artificial Sequence
<220> FEATURE:
<223> OTHER INFORMATION: bacterial consensus sequence

<400> SEQUENCE: 17 uuuggauaa                                                                 9

<210> SEQ ID NO 18
<211> LENGTH: 9
<212> TYPE: DNA
<213> ORGANISM: Artificial Sequence
<220> FEATURE:
<223> OTHER INFORMATION: bacterial consensus sequence

<400> SEQUENCE: 18 aaacctatt                                                                 9

<210> SEQ ID NO 19
<211> LENGTH: 10
<212> TYPE: RNA
<213> ORGANISM: Artificial Sequence
<220> FEATURE:
<223> OTHER INFORMATION: bacterial consensus sequence

<400> SEQUENCE: 19
ccaauaugug                                                               10
```

```
<210> SEQ ID NO 20
<211> LENGTH: 10
<212> TYPE: DNA
<213> ORGANISM: Artificial Sequence
<220> FEATURE:
<223> OTHER INFORMATION: bacterial consensus sequence

<400> SEQUENCE: 20
ggttatacac                                                           10

<210> SEQ ID NO 21
<211> LENGTH: 11
<212> TYPE: RNA
<213> ORGANISM: Artificial Sequence
<220> FEATURE:
<223> OTHER INFORMATION: bacterial consensus sequence

<400> SEQUENCE: 21
gguuauacca c                                                         11

<210> SEQ ID NO 22
<211> LENGTH: 11
<212> TYPE: DNA
<213> ORGANISM: Artificial Sequence
<220> FEATURE:
<223> OTHER INFORMATION: bacterial consensus sequence

<400> SEQUENCE: 22
ccaatatggt g                                                         11

<210> SEQ ID NO 23
<211> LENGTH: 9
<212> TYPE: RNA
<213> ORGANISM: Artificial Sequence
<220> FEATURE:
<223> OTHER INFORMATION: bacterial consensus sequence

<400> SEQUENCE: 23 acaccuauu                                                             9

<210> SEQ ID NO 24
<211> LENGTH: 9
<212> TYPE: DNA
<213> ORGANISM: Artificial Sequence
<220> FEATURE:
<223> OTHER INFORMATION: bacterial consensus sequence

<400> SEQUENCE: 24 tgtggataa                                                             9

<210> SEQ ID NO 25
<211> LENGTH: 9
<212> TYPE: RNA
<213> ORGANISM: Artificial Sequence
<220> FEATURE:
<223> OTHER INFORMATION: bacterial consensus sequence

<400> SEQUENCE: 25 uguggauaa                                                             9

<210> SEQ ID NO 26
<211> LENGTH: 9
<212> TYPE: DNA
<213> ORGANISM: Artificial Sequence
<220> FEATURE:
<223> OTHER INFORMATION: bacterial consensus sequence
```

```
<400> SEQUENCE: 26 acacctatt                                                                9

<210> SEQ ID NO 27
<211> LENGTH: 9
<212> TYPE: RNA
<213> ORGANISM: Artificial Sequence
<220> FEATURE:
<223> OTHER INFORMATION: bacterial consensus sequence
<220> FEATURE:
<221> NAME/KEY: misc_feature
<222> LOCATION: (5)..(5)
<223> OTHER INFORMATION: n is a, c, g, or u

<400> SEQUENCE: 27 aauangugu                                                                9

<210> SEQ ID NO 28
<211> LENGTH: 9
<212> TYPE: DNA
<213> ORGANISM: Artificial Sequence
<220> FEATURE:
<223> OTHER INFORMATION: bacterial consensus sequence
<220> FEATURE:
<221> NAME/KEY: misc_feature
<222> LOCATION: (5)..(5)
<223> OTHER INFORMATION: n is a, c, g, or t

<400> SEQUENCE: 28 ttatncaca                                                                9

<210> SEQ ID NO 29
<211> LENGTH: 9
<212> TYPE: RNA
<213> ORGANISM: Artificial Sequence
<220> FEATURE:
<223> OTHER INFORMATION: bacterial consensus sequence
<220> FEATURE:
<221> NAME/KEY: misc_feature
<222> LOCATION: (5)..(5)
<223> OTHER INFORMATION: n is a, c, g, or u

<400> SEQUENCE: 29 uuauncaca                                                                9

<210> SEQ ID NO 30
<211> LENGTH: 9
<212> TYPE: DNA
<213> ORGANISM: Artificial Sequence
<220> FEATURE:
<223> OTHER INFORMATION: bacterial consensus sequence
<220> FEATURE:
<221> NAME/KEY: misc_feature
<222> LOCATION: (5)..(5)
<223> OTHER INFORMATION: n is a, c, g, or t

<400> SEQUENCE: 30 aatangtgt                                                                9
```

POLYNUCLEOTIDES THAT STIMULATE NEUTROPHILS

CROSS-REFERENCE TO RELATED APPLICATIONS

This application claims priority under 35 U.S.C. §119 to provisional application Ser. No. 61/314,368 filed Mar. 16, 2010, herein incorporated by reference in its entirety.

FIELD OF INVENTION

The present invention relates to polynucleotides that are fully or partially complementary to the Initiation Sites within the Origins of Replication found in microbial genomes or to DnaA. The DNA sequences in the microbial world of bacteria, fungi and viruses are similar with a well-conserved core. These nucleotides are released within minutes by invading microbes, triggering their maximum growth and mutation rates. Through co-evolution, these nucleotides alert sentry cells of the immune system to heighten an attack against microbes and to send alerting signals downstream throughout the immune network. The ability of test nucleotides to restore or enhance an immune response can be determined by exposing them to neutrophils in cell culture.

BACKGROUND OF THE INVENTION

The environment contains a variety of microbes, such as viruses, bacteria, fungi and parasites, any number of which can infect a host and cause pathological damage or cause the immune system to turn on itself. One example of such a microorganism is *Klebsiella pneumoniae*, an encapsulated, highly virulent Gram-negative bacteria that is a leading cause of both community-acquired and nosocomial pneumonia. *K. pneumoniae* can also spread from the lung into the bloodstream, resulting in widespread systemic dissemination and death.

Most organisms, such as mammals, i.e. humans, have developed an immune system to ward off such infections. The immune system is divided into two functional divisions, the innate immune system and the adaptive immune system. The innate and adaptive immune system consists of a variety of molecules and cells distributed throughout the body. The most important cells are leukocytes, which are categorized as phagocytes, including polymorphonuclear neutrophils (PMNs), monocytes and macrophages, and lymphocytes, which mediate adaptive immunity. The two main phagocytic cells that constitute pulmonary innate immunity are resident alveolar macrophages (AM) and recruited neutrophils (PMN) (Lipscomb et al., 1983; and Towes et al., 1980).

Inflammation is the body's response to invasion by an infectious microbial agent and includes three broad actions. First, the blood supply is increased to the area. Second, capillary permeability is increased, thereby permitting cells and larger molecules to reach the site of infection. Third, leukocytes, particularly PMNs, migrate out of the capillaries and into the surrounding tissue. Once in the tissue, the PMNs migrate to the site of infection or injury by chemotaxis. These events manifest themselves as inflammation.

Once at the site of infection, PMNs perform phagocytic and degradative functions to combat the infectious agent. As part of the response to the infectious agent, PMNs and activated macrophages rapidly consume oxygen in the "respiratory burst" and convert it to superoxide anion and subsequently hydrogen peroxide ($H_2O_2$), as well as significant amounts of singlet oxygen to kill infested material and adhere to epithelial cells of mucosal surfaces or vascular endothelial cells of the blood vessels. In some cases, the immune system of the host fails to mount a successful response and needs help in this regard. For these and other reasons, there is a need for the present invention.

U.S. Pat. Nos. 5,840,318 and 7,189,834 and 7,678,557 describe the fermentation and processing conditions to yield populations of harmless bacteria which have accumulated and retained significant levels of oligoribonucleotides (ORNs) smaller than 10 kDa, ORN<10 kDa which are released during invasion. An animal's immune system can be stimulated by feeding such bacteria or a preparation of the released ORN<10 kDa which contain the stimulating oligos. In addition, ORN<10 kDa can be injected without adverse visible side effects. Such treatments have been shown to significantly reduce the lethality of septic shock in mice and viral infections in shrimp and beef. See U.S. Pat. No. 5,840,318.

U.S. Pat. No. 7,678,557 describes that when bacteria are grown naturally without the usual commercial addition of base to maintain a neutral pH and high growth rates, the bacteria accumulate stimulating ORNs. Microbes release these ORNs as a survival response when entering physiological conditions e.g., saliva and its neutral pH.

For these and other reasons, there is a need for the present invention.

BRIEF SUMMARY OF THE INVENTION

In one aspect the present invention relates to a method of treating or preventing a microbial infection. The method includes administering the animal in need thereof a therapeutically effective amount of a polynucleotide complementary to a portion of an Initiation Site of an Origin of Replication of a microbe.

In a further aspect the present invention relates to a method for stimulating the immune system of an animal. The method includes contacting a neutrophil in an animal with a therapeutically effective amount of a polynucleotide complementary to a portion of an Initiation Site of an Origin of Replication of a bacterium, so that an immune system's genetic potential is restored.

The present invention yet further provides a method of stimulating a neutrophil. The method includes contacting a neutrophil with an effective amount of a polynucleotide complementary in part or fully to a portion of an Initiation Site of an Origin of Replication of a bacterium for a sufficient amount of time to stimulate the neutrophil.

In another aspect the present invention provides an isolated polynucleotide having a sequence of about 5 to about 15 nucleotides in length sufficiently complementary to a portion of an Initiation Site of an Origin of Replication of a bacterium to stimulate the neutrophil.

In a further aspect the present invention provides a pharmaceutical composition that includes an effective amount of the polynucleotide of the present invention and a carrier. In a yet another aspect, the present invention provides an immune-enhancing animal feed or drinking water composition for animal consumption comprising an animal feed or drinking water and an effective amount of the polynucleotide the present invention.

The foregoing and other aspects of the invention will become more apparent from the following detailed description.

DETAILED DESCRIPTION OF THE PREFERRED EMBODIMENT

All references referred to are incorporated herein by reference.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not intended to limit the scope of the invention.

As used herein, the following phrases and terms are defined as follows:

An Arbitrary Unit of 1 is a reading at 254 nm of 1.000. An AU of 1, corresponding to about 35 μg of ribonucleotides, is released by 1–3×10e9 CFUs of bacteria grown and processed according to U.S. Pat. No. 7,678,557.

Dendritic cells are cells of the immune network whose role is to survey local environments and ingest pathogens. They have receptors on their surfaces that recognize common features of bacteria. Binding of a bacterium to a receptor stimulates the dendritic cell to release cytokine messages and engulf the pathogen.

Neutrophils are stimulated by the presence of bacteria to kill pathogens by a burst of oxidative products lethal to bacteria.

Phorbol Myristic Acetate is a well-known stimulator of the oxidative burst of neutrophils. However, it is toxic.

A=adenine, C=cytosine, G=guanine, T=thymine

An "isolated polynucleotide" is a polynucleotide whether naturally occurring synthesized or recombinant, whether purified or not. Optionally, an isolated polynucleotide is subject to one or more enrichment or purification procedures, e.g., cell lysis, extraction, centrifugation, precipitation, concentration, exposure to neutral pH, or the like.

The term "Initiation Site" shall mean the region within an Origin of Replication on the genome of microbes, which is associated with replication. DnaA is a protein that plays a key role in initiating the replication of the entire genome by binding to a specific sequence of about 12 nucleotides in the site. Complementary to their sequence are 15-20 amino acids in DnaA which bind to all or part of the 12 nucleotides. Genera and species of bacteria are known to have about 5 to 19 Initiation Sites on their genomes with slightly differing nucleotide sequences. DnaA therefore exhibits different affinities toward the various sites. However certain core sequences of nucleotides appear in all Initiation Sites.

The term "stimulates" means promoting or increasing of the activity of a neutrophil, e.g. generation of active oxygen species and/or increasing oxidative burst. The promoting or increasing of an activity of a neutrophil can occur by contacting a neutrophil with an effective amount of a polynucleotide of the present invention.

As used herein, "stimulating an animal's immune response" means increasing the host's ability to retain homeostasis and successfully fight off an infection. Stimulation can be measured by the end effect of protection or by the amount of a component of the immune system or the activity by which a component of the immune system is characterized, increasing the amount of receptor present on the surface of an immune cell, or increasing the number of immune cells present in the animal.

The term "pharmaceutical composition" comprises one or more polynucleotides of the present invention as active ingredient(s) and may also contain a pharmaceutically acceptable carrier and optionally other therapeutic ingredients. The compositions include compositions suitable for various routes of administration which are described elsewhere herein. The most suitable route in any particular case will depend on the nature and severity of the disease, disorder, or conditions being treated. The compositions may be presented in unit dosage form and prepared by any of the methods well-known in the art of pharmacy. Dosage regimes may be adjusted for the purpose to improving the therapeutic response. For example, several divided dosages may be administered daily or the dose may be proportionally reduced over time. A person skilled in the art normally may determine the effective dosage amount and the appropriate regime.

The term "animal" is intended to include living organisms, in particular, those with vertebrates, such as human, livestock or farm animals, or companion animals. Examples of animals include warm blooded animals, more preferably mammals such as humans, dogs, cats, cows, goats, and mice or cold blooded animals such as fish or shrimp and the like.

The term "ameliorate" is intended to include treatment for, prevention of, limiting of and/or inhibition of undesired microbial infections or causing the regression of the disease, disorder, or condition caused by the microbial infection. It also refers to the re-establishing the status quo of an immune system thereby preventing shock, when the immune system turns on the host and destroys it by fevers and internal bleeding.

As used herein, "therapeutically effective amount" refers to an amount, which is effective in reducing, eliminating, treating, preventing or controlling the symptoms of the herein-described diseases, disorders, or conditions, for example, a therapeutically effective amount of polynucleotides of the present invention will provide protection against endotoxemia. The effective amount of nucleotides either fed or injected will depend on the state of vigor or health of the animal's immune system versus the virulence or toxicity of the microorganism.

As used herein, unless otherwise defined in conjunction with specific diseases or disorders, the term "treating" refers to: (i) preventing a disease, disorder or condition from occurring in an animal or human that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

The terms "enhancing the immune system" or "immune-enhancing" as used herein includes (1) stimulating an animal's immune system to provide protection against microbial invasions, the lethality of toxins, e.g., endotoxemia, and the occurrence of auto-immune diseases as well as other diseases symptomatic of an unrestrained immune system; (2) stimulating an animal's immune system to its highest potential so that the immune system responds to an infection at its complete power; (3) modulating an animal's immune system to adjust the expression of individual surface receptors on macrophages to re-center a dysfunctional immune system; (4) modulating an animal's immune system to rescue monocytes from apoptosis; and (5) stimulating macrophages to release interleukins and down regulate surface receptors, (6) neutrophil function in vitro, in vivo, or ex vivo so that a neutrophil is stimulated to increase oxygen uptake and/or release oxidative factors; (7) stimulating dendritic cells to release signaling Interleukins; (8) acting like adjuvants by increasing production of antibodies to a known antigen; and/or (9) modulating or preventing an immune system under attack from going awry and causing the death of the host.

I. Introduction

DNA replication in bacteria begins with the formation of a tetramer of the protein DnaA which binds to one or several Initiation Sites in the Origin of Replication, oriC. (*Physiology of the Bacterial Cell—A Molecular Approach*, p 401, Neidhardt, F. C., Ingraham, J L, Schaechter, M., Sinauer Press, 1990.)

The invention described herein is based on the surprising finding that polynucleotides complementary to Initiation Sites or to the consensus core of the Initiation Sites found in the Origins of Replications of a bacterium stimulate neutrophils, a key sentry cell of the immune network.

The consensus core is the shortest DNA sequence that appears in the Initiation Site on the genomes of many species of microbes is: 5'TTATCCACA3', SEQ ID NO:1 and, on the opposing strand: 5'AATAGGTGT3', SEQ ID NO:2. Polynucleotides complementary to these core sequences are used by bacteria to prevent the binding of their DnaA, thereby down-regulating their DNA replication. Two such ribonucleotides, 5'UUAUCCACA3', SEQ ID NO:29 and for the opposing strand: 5'AAUAggUgU3', SEQ ID NO:27 provide the greatest stimulus to neutrophils.

Neutrophils are either imbedded in tissue, e.g. the oropharyngeal cavity, or circulating in the blood, searching out sites inflamed by infection.

The consensus core, or parts thereof, is found in the Initiation Sites across bacteria, fungi and viruses. Since all animals are exposed to similar microbes one would expect an immune system stimulated by treatment with polynucleotides of the present invention that are complementary to the consensus sequence of Initiation Sites to be protected against a variety of microbial infections. Without wishing to be bound by this theory it may explain why protection in a variety of animal species such as mice, shrimp and cattle administered polynucleotides of the present invention have been observed.

Example 1 shows that both Oligos A and B stimulate neutrophils at very low concentrations. Oligos A and B are complementary to the DNA sequence most commonly found in microbes. They are complementary to the two opposing strands of DNA in the Initiation Sites. Individually and together they stimulate neutrophils from very low to high concentrations. The results indicate that neutrophils have receptors to single ribonucleotides strands yet are able to responds somewhat to homo- and hetero-dimers. Oligo A forms a dimer with itself which may provide protection against phagocytosis. The stimulation of neutrophils as shown by the transient increase in oxygen uptake and release of reactive oxygen species (superoxide) represents one of the major systems through which polymorphonuclear leukocytes (neutrophils) kill invading organisms.

The stimulation of neutrophils is recorded by measuring the transient increase in oxygen uptake and release of reactive oxygen species (superoxide) represents one of the major systems through which polymorphonuclear leukocytes (neutrophils) kill invading organisms.

Accordingly, the polynucleotides, compositions and methods of the present invention may be used to enhance or stimulate the immune response or system of an animal, e.g. to prevent an infection caused by a microorganism, ameliorate an infection caused by a microorganism, or kill an invading microorganism that causes infection. In particular, the polynucleotides, compositions and methods of the present invention may be used to treat or prevent bacterial infection in a mammal in need thereof. Bacterial infections can or contribute to a variety of diseases, disorders or conditions including various forms of endocarditis, osteomyelitis, meningitis, skin and skin structure infections, pneumonias, bacteremias, intra-abdominal infections, genitourinary tract infections, abscesses, and necrotizing infections. Included within the present invention are responses to other types of infections caused by other microorganisms, such as viruses, fungi and the like as well as to chemical toxins, e.g. lipopolysaccharide and prions.

Provided herein are polynucleotides that stimulate or increase neutrophil function. Accordingly, neutrophils may be contacted with an effective amount of one or more polynucleotides of the present invention and/or compositions comprising polynucleotides of the present invention for a sufficient amount of time to stimulate neutrophil function. As used herein, "neutrophil function" refers to a neutrophil the ability of a neutrophil to uptake oxygen, e.g. experience a transient increase in oxygen uptake, and/or to release of reactive oxygen species and the protein myeloperoxidase.

Polynucleotides of the present invention and/or compositions comprising polynucleotides of the present invention may be used to enhance or stimulate the immune system or immune response of animal in need thereof. For example, to prevent or ameliorate a bacterial infection in an animal or kill bacteria.

II. Polynucleotides

Any polynucleotide that is complementary to the sequence of all or part of an Initiation Site of Origin of Replication of a bacterium, yeast or virus and stimulates neutrophil functions may be employed in the present invention. A "polynucleotide" is a single- or double-stranded polymer of deoxynucleotide or ribonucleotide bases read from the 5' to the 3' end.

A polynucleotide of the present invention is complementary to an Initiation Site of a bacterium's Origin of Replication. The term "complementary" or "complementarity" as used herein with respect to polynucleotides or oligonucleotides, which terms are used interchangeably herein, refers to the ability of nucleic acid bases of an individual polynucleotide of the present invention to preferably form Watson-Crick base pairing in an anti-parallel fashion with nucleic acid bases of a nucleic acid having the Initiation Site of a replication of origin, e.g. via Watson-Crick pairing (A opposite U or T, and G opposite C). For example, 5, 6, 7, 8, 9, or 10 nucleotides out of a total of 10 nucleotides in the first oligonucleotide forming Watson-Crick base pairing with a second nucleic acid sequence having 10 nucleotides represents 50%, 60%, 70%, 80%, 90%, and 100% complementarity respectively.

A polynucleotide of the present invention that is complementary to an Initiation Site of a bacterium's Origin of Replication may also include "non-canonical base pairing" such as non-Watson Crick base pairing, such as mismatches and/or wobble base pairs, including flipped mismatches, single hydrogen bond mismatches, trans-type mismatches, triple base interactions, and quadruple base interactions. Accordingly, nucleic acid bases of an individual polynucleotide of the present invention that form non-Watson-Crick base pairing (non-canonical base pairing) in an anti-parallel fashion with nucleic acid bases of a nucleic acid having the Initiation Site of a replication of origin so long as the polynucleotide has the ability to stimulate neutrophils. Non-limiting examples of such non-canonical base pairs include, but are not limited to, AC reverse Hoogsteen, AC wobble, AU reverse Hoogsteen, GU wobble, AA N7 amino, CC 2-carbonyl-amino(H1)-N-3-amino(H2), GA sheared, UC 4-carbonyl-amino, UU iminocarbonyl, AC reverse wobble, AU Hoogsteen, AU reverse Watson Crick, CG reverse Watson Crick, GC N3-amino-amino N3, AA N1-amino symmetric, AA N7-amino symmetric, GA N7-N1 amino-carbonyl, GA+carbonyl-amino N7-NI, GG N1-carbonyl symmetric, GG N3-amino symmetric, CC carbonyl-amino symmetric, CC N3-amino symmetric, UU 2-carbonyl-imino symmetric, UU 4-carbonyl-imino symmetric, AA amino-N3, AA N1-amino, AC amino 2-carbonyl, AC N3-amino, AC N7-amino, AU amino-4-carbonyl, AU N1-imino, AU N3-imino, AU N7-imino, CC carbonyl-amino, GA amino-N1, GA amino-N7, GA carbonyl-amino, GA N3-amino, GC amino-N3, GC carbonyl-amino, GC N3-amino, GC N7-amino, GG amino-N7, GG carbonyl-imino, GG N7-amino, GU amino-2-carbonyl, GU carbonyl-imino, GU imino-2-carbonyl, GU N7-imino, psiU imino-2-carbonyl, UC 4-carbonyl-amino, UC imino-carbonyl, UU imino-4-carbonyl, AC C2-H-N3, GA carbonyl-C2-H, UU imino-4-carbonyl 2 carbonyl-05-H, AC amino(A) N3(C)-carbonyl, GC imino amino-carbonyl, Gpsi imino-2-carbonyl amino-2-carbonyl, and GU imino amino-2-carbonyl base pairs.

A sequence that is complementary to another sequence is also referred to as the complement of the other. As used herein with respect to determining complementarity of a polynucleotide sequences of the present invention with an Initiation Site sequence, the bases thymidine ("T") and uridine ("U") are frequently interchangeable depending on the source of the sequence information (DNA or RNA). Therefore, the base "T" is fully interchangeable with the base "U".

As the skilled artisan will appreciate, complementarity, where present, can be partial or full. "Partial complementarity" or "partially complementary" as used herein indicates that only a percentage of the contiguous residues of a nucleic acid sequence can form Watson-Crick base pairing with the same number of contiguous residues in a second nucleic acid sequence in an anti-parallel fashion. Partially complementary means that in comparing the polynucleotide sequence with the initiation sequence there are 1, 2, 3, 4, 5, 6, 7, 8, 9, 10 or more mismatches between the pair of sequences according to the canonical base pairing rules. For example, the sequence 5'UUAUXCACA3', SEQ ID NO:29, wherein X is G or C is partially complementary to 5'AATAXCGCG3', SEQ ID NO:30.

The DnaA tetramer strongly binds the DNA sequence 5'TTATXCACA3', SEQ ID NO:5 (X can be C or G). The 6 Initiation Sites in the leading strand of *E. coli* contain: 5'TTATCCACA3', SEQ ID NO:1, 5'TTTGGATAA3', SEQ ID NO:2, 5'GGTTATACAC3', SEQ ID NO:3 and 5'TGTGGATAA3', SEQ ID NO:4 with complementary sequences in the opposing or lagging strand. Parts of these sequences are also found in the Initiation Sites of *H. pylori* and *M. tuberculosis:* 5'TTATxCACA3', SEQ ID NO:5 and in their lagging strand 5'AATAxGTGT3'. (Architecture of Bacterial Replication Initiation Complexes: Orisomes from Four Unrelated Bacteria, Biochem. J. (2005) 389, 471-481, Zawilak-Pawlik, A. et al.).

To date, the DNA sequences in known Initiation Sites within the Origins of Replication of several bacteria are:

| Leading Strand | |
|---|---|
| 5'TTATCCACA3', | SEQ ID NO: 1 |
| 5'TTTGGATAA3', | SEQ ID NO: 2 |
| 5'GGTTATACAC3', | SEQ ID NO: 3 |
| 5'TGTGGATAA3', | SEQ ID NO: 4 |
| 5'TTATxCACA3', | SEQ ID NO: 5 |
| Following Strand | |
| 5'AATAGGTGT3', | SEQ ID NO: 6 |
| 5'AAACCTATT3', | SEQ ID NO: 7 |
| 5'CCAATATGGTG3', | SEQ ID NO: 8 |
| 5'ACACCTATT3', | SEQ ID NO: 9 |
| 5'AATAxGTGT3', | SEQ ID NO: 10 |

Therefore, it is anticipated that the following sequences of ORN will bind complementarily to these 10 DNA sequences. As used herein "fully complementarity" or "fully complementary" indicates that all the contiguous residues of a nucleic acid sequence can form Watson-Crick base pairing with the same number of contiguous residues in a second nucleic acid sequence in an anti-parallel fashion. A sequence that is fully complementary to another sequence is also referred to as the complete complement of the other.

| | ORN Sequence | Binding to DNA sequence |
|---|---|---|
| a. | 5'AAUAGGUGU3', SEQ ID NO: 11 | 5'TTATCCACA3', SEQ ID NO: 12 |
| b. | 5'UUAUCCACA3', SEQ ID NO: 13 | 5'AATAGGTGT3', SEQ ID NO: 14 |
| c. | 5'AAACCUAUU3', SEQ ID NO: 15 | 5'TTTGGATAA3', SEQ ID NO: 16 |
| d. | 5'UUUGGAUAA3', SEQ ID NO: 17 | 5'AAACCTATT3', SEQ ID NO: 18 |
| e. | 5'CCAAUAUGUG3', SEQ ID NO: 19 | 5'GGTTATACAC3', SEQ ID NO: 20 |
| f. | 5'GGUUAUACCAC3', SEQ ID NO: 21 | 5'CCAATATGGTG3', SEQ ID NO: 22 |
| g. | 5'ACACCUAUU3', SEQ ID NO: 23 | 5'TGTGGATAA3', SEQ ID NO: 24 |
| h. | 5'UGUGGAUAA3', SEQ ID NO: 25 | 5'ACACCTATT3', SEQ ID NO: 26 |
| i. | 5'AAUAxGUGU3', SEQ ID NO: 27 | 5'TTATxCACA3', SEQ ID NO: 28 |
| j. | 5'UUAUxCACA3', SEQ ID NO: 29 | 5'AATAxGTGT3', SEQ ID NO: 30 |

These sequences are well conserved across the microbial world. Mutations in DnaA seemed to be able to be accommodated by the near-universal sequences mentioned above. The consensus sequence is Oligo B, 5'UUAUCCACA3', SEQ ID NO:13 in Example 1. Shorter consensus complementary sequences are 5'AAUA3' and 5'UUAU3'.

Since biological systems have multiple layers of check and balances, anti-idiotypes of either deoxynucleotides or ribonucleotides to the stimulating ORNs are likely made by the bacterial cell to balance the effects of the rate-retarding ORN.

Neutrophils are among the cells that represent the host's first line of cell defense. They belong to a family of immune sentry cells defending against bacterial, viral and fungal infections Like other phagocytic sentry cells, neutrophils can be imbedded in tissues or move among the spaces in tissues. In addition, neutrophils, circulating in the blood, quickly invade tissues inflamed by infection. The interstitial spaces are opened, allowing them to reach the nidus of infection where they engulf the microbe into a vacuole and bombard it with reactive oxygen intermediates, such as superoxides, hydrogen peroxide and hydroxyl radicals. Anti-microbial proteins and bactericidal enzymes like myeloperoxidase are also employed.

Examples of ribonucleotides partially complementary to Initiation Sites and DnaA include but are not limited to 5' UAUU 3', 5' CCACA3', 5' AAUA 3', 5' GGUGU 3', 5' UUAUA 3', 5' UUA 3', 5'AUAA 3', 5'UUAU 3', 5'AAA 3', 5' UUU 3', 5' AAUA 3', 5'UUAU 3', 5' AUAA 3', 5' UAUU 3', 5' AAUAU 3', and 5' UUAUA 3'. 5'UGUG'3.

Examples of deoxynucleotides complementary to Initiation Sites and DnaA include but are not limited to 5' TATT 3', 5' AATAT 3', 5' AAA 3', 5' TATT 3', 5' AATA 3', 5' ATAA 3', 5' TTATA3', 5' TTT 3', 5' ATAA 3', 5' TTAT 3', 5' AAA 3', 5' TTT 3', 5' AATA 3', 5' TTAT 3', 5' ATAA 3', 5' TATT 3', 5' AATAT 3', and 5' TTATA 3'.

In some examples, the polynucleotides are complementary to a portion of the bacterial Initiation Site in the Origin of Replication, for example, over a portion of at least about 5, 6, 7, 8, 9, 10, 11, 12, 13, 14, 15 or more nucleotides of the Initiation Site or complementary to the entire sequence of the Initiation Site. The percentage of complementarity between the polynucleotide sequence and the Initiation Site sequence can be evaluated by sequence base-pairing between the polynucleotide sequence and the Initiation Site sequence. In some examples, the polynucleotides are partially complementary to a portion of the Initiation Site or across the entire Initiation Site. For example, the sequence may be 50%, 60%, 70%, 80%, 90%, 91%, 92%, 93%, 94%, 95%, 96%, 97%, 98%, or 99% complementary to the portion of the Initiation Site or entire Initiation Site. In some cases, the sequences are fully complementary (100% complementary) to the sequence of a portion of the Initiation Site or entire Initiation Site.

In addition to the foregoing, the skilled artisan will appreciate that in some instances the polynucleotides may be shorter or longer in the length than the sequence of the Initiation Site. Typically the polynucleotides are 5, 6, 7, 8, 9, 10, 11, 12, 13, 14, 15, 16, 17, 18, 19 or more consecutive polymerized nucleotides (nt) in length. Sizes of polynucleotides are expressed as base pairs (abbreviated "bp"), nucleotides ("nt"), or kilobases ("kb"). Polynucleotides can vary in size from as few as 3 bases to the full length of the Initiation Site, but are preferably at least about 9 bases in length.

For example, a polynucleotide may be partially or fully complementary, with respect to a portion or the entire Initiation Site and still contain additional bases at the 5' and/or 3' end. In other examples, the polynucleotides may be partially or fully complementary with a portion of the Initiation Site and contain deletions of bases from the 5' and/or 3' end of the polynucleotide sequence. In some cases, the polynucleotides are a subsequence of the consensus core polynucleotide. Exemplary sequences include 5'UUAU3' and 5'AAUA3'.

Polynucleotides of the present invention also include those that differ from the presently disclosed polynucleotides and include those with substitutions, deletions, insertions or any combination thereof into a sequence of a polynucleotide that is complementary to an Initiation Site. Such modifications (substitutions, deletions, insertions) can be achieved using any suitable means or techniques such as site-directed mutagenesis, PCR or synthetic chemistry. (Wu (ed.) Methods Enzymol. (1993) vol. 217, Academic Press). The modifications that are made in the polynucleotide should not affect the ability of the polynucleotide to stimulate neutrophil function.

Polynucleotides may also include subsequences of polynucleotides.

The polynucleotide of the present invention may be produced by any suitable means. Polynucleotides may be isolated from natural sources, synthesized in vitro, prepared using chemical synthesis, or any combination thereof. The polynucleotide may be isolated, cloned, or synthesized and, if desired, inserted into any of the many available expression vectors and cell systems using reagents well known in the art. For example, the polynucleotide can be cloned into a vector or plasmid or other construct, such as a cosmid, a phage, a virus, a bacterial artificial chromosome (BAC), a yeast artificial chromosome (YAC), or the like, into which a polynucleotide sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

A polynucleotide of the present invention is complementary to the Initiation Site of the bacterium's Origin of Replication. The Initiation Site of the bacterium's Origin of Replication may be from any bacterium. The bacterium may belong to any phylum, class, order, family, genus or species. Exemplary genera include but are not limited to bacteria from *Mycobacteria, Chlamydia, Helicobacter, Lactobacillus, Staphylococcus, Streptococcus, Pediococcus, Pseudomonas, Bacillus, Escherichia, Listeria, Enterococcus, Klebsiella, Borrelia, Yersinia*, influenza viruses, West Nile virus, *Bartonella, Ehrlichia, Rickettsia, Legionella, Haemophilus*. Exemplary species include *Mycobacterium tuberculosis, Mycobacterium avium complex, Chlamydia pneumoniae, Helicobacter pylori, L. acidophilus, L. caseii, L. fermentum, L. plantarum, L. monocytogenes, L. innocua, S. aureus, S. typhimurium, P. acidolactici, B. coryneforme, E. coli, E. faecium, S. pyogenes*, and *K. pneumonia, B. henselae, R. typhi, B. burgdorferi, H. influenzae, L. pneumophila, E. chaffeenis*, or *R. parkeri*.

A variety of Initiation Sites are known and can be used in the methods and compositions described herein. The sequences of various Initiation Sites are disclosed in the literature and Genbank, among other public sources, and may be obtained by cloning, PCR, from deposited materials or any other suitable technique. Examples of public databases that include sequences of Initiation Sites include: Genbank: dbESTncbi.nlm.nih.gov/genbank/:EMBL:ebi.ac.uk.embl/: BLAST, PubMed.com; Nucleotide and Protein databases, PubMed.com as well as, e.g., Brookhaven Laboratories; the University of Wisconsin Biotechnology Center, the DNA databank of Japan, Laboratory of genetic Information Research, Misuina, Shizuda, Japan.

III. Testing of Polynucleotides of the Present Invention

Polynucleotides complementary to the Initiation Site of the Origin of Replication may be tested for their ability to stimulate neutrophils, e.g. to stimulate neutrophils to release oxidative factors or transient increase in oxygen uptake (respiratory burst), as described elsewhere herein or using other techniques known to one skilled in the art.

Polynucleotides that stimulate neutrophils may be identified by exposing neutrophils isolated from the kidneys of fathead minnows to one or more polynucleotides complementary to an Initiation Site of Origin of Replication. The oxidation of the non-fluorescent dihydrorhodamine 123 (DHR123) to fluorescent rhodamine (Rh 123) may be determined indirectly by determining fluorescence intensity using spectrofluorometry in a flow cytometer. Rh 123 has an absorption maximum at 507 nm and a fluorescence maximum at 529 nm. Results of fluorescence intensity for the polynucleotide of the present invention and a control may be obtained and compared. The control serves as a reference point for measuring changes in phenotype such as fluorescence intensity. A control may include a neutrophil contacted with a known neutrophil stimulator, such as phorbol myristic acetate (PMA), and/or a neutrophil not exposed to the neutrophil stimulator or the polynucleotide of the present invention. The degree or amount of fluorescent intensity of each sample may be determined at a desired time point and the values of various samples compared. For example, a similar or an increase in the fluorescence intensity level of a sample from a neutrophil exposed to a polynucleotide of the present invention relative to the fluorescence intensity level of a sample from a neutrophil exposed to a known neutrophil stimulator would be indicative of the polynucleotide being able to stimulate neutrophils. For example, an increase in the fluorescence intensity level of a sample from a neutrophil exposed to a polynucleotide of the present invention relative to the fluorescence intensity level of a sample from a control neutrophil not exposed a known neutrophil stimulator or polynucleotide of the present invention would be indicative of the polynucleotide being able to stimulate neutrophils. Other suitable assays may be used to determine neutrophil stimulation, by measuring the uptake of oxygen or destruction of bacteria, including but not limited to. Measuring the release of specific cytokines can also be used to determine neutrophil activity. See: Scapini, P., Llapinet-Vera, J., Gasperini, S., Calzetti, F., Bazzoni, F., Cassatella, M., The Neutrophil as a Cellular Source of Cytokines; Immunol. Rev. 177, 195-203.

Polynucleotides that stimulate neutrophils may be employed to modify an animal's immune system or immune response, for example, enhance an animal's immune system or immune response.

IV. Feed

Also provided herein are methods for preparing an animal feed or animal drinking water comprising polynucleotides of the present invention. The polynucleotides of the present invention can be added to any animal feed or supplement for livestock or companion animals including, but not limited to, grains or pelleted concentrates, including those commercially available. In addition, the polynucleotides of the present invention may be incorporated directly into drinking-water, animal feeds or feed supplements, including those feeds that are commercially available. When incorporated directly into animal feeds or drinking water, the present invention may be added to such feeds or waters in amounts determined by small scale experimentation deliver an effective dose. An effective dose depends on the strength of the animal's immune response and the degree of virulence of the pathogen, similar to the logic used in prescribing the effective doses of antibiotics. However, one can expect the effective dose to be in the range of 0.2-280 µg of polynucleotide per animal per day. Neonatal animals, without mature immune systems will not benefit from treatments with complementary nucleotides.

In addition, to prevent an immune system from going awry or attacking itself, the effective dose is given before the immune disrupting shock, between 18 and 72 hr in advance. The amount of polynucleotides of the present invention, e.g. oligoribonucleotides, can be calculated using any suitable method, for example, it may be determined based on the relationship between optical density (OD), absorbance (A) and arbitrary units (AU) so that the amount of ORN can be determined as µg/mL. An OD unit corresponds to the amount of nucleic acid in 35 µg in a 1 mL volume using a 1 cm path length quartz cuvette that results in an $OD_{254}$ reading of 1.

The polynucleotides of the present invention may be admixed with animal feed, or sprayed onto extruded pellets or added to the animals' drinking water or as a gel to be administered directly into the animal's mouth as a supplement. In another aspect, the polynucleotides of the present invention, preferably purified and isolated, can be stored frozen or as a freeze-dried powder, stable for 4-6 mo. and 4-8 weeks at room temperature.

V. Pharmaceutical Compositions

As mentioned above, the compositions of the present invention may be used in the treatment and/or prophylaxis of any of a variety of diseases, disorders, or conditions in which involvement of neutrophil stimulation is desired, including bacterial infections, etc. In addition, they may be used for a variety of other purposes in which it is desired to inhibit replication of the bacteria in vitro, ex vivo, or in vivo in an animal.

In one aspect, a composition for use in the methods described herein include a polynucleotide complementary to an Initiation Site of an Origin of Replication or its dnaA proteins and stimulates neutrophil function. A pharmaceutical composition is also provided. Accordingly, the pharmaceutical composition may comprise a polynucleotide of the present invention and optionally a pharmaceutically acceptable carrier. The pharmaceutical composition may be administered by any suitable known methods or technique. Commonly used gene transfer techniques include calcium phosphate, DEAE-dextran, electroporation, microinjection, viral methods and cationic liposomes and vectors.

In an in vivo approach, a polynucleotide of the present invention is administered to a subject such as an animal. Generally, the polynucleotide of the present invention is in a pharmaceutically-acceptable carrier (e.g., physiological saline). A composition of the present invention, such as a pharmaceutical composition, may comprise different types of acceptable carriers depending on whether it is to be administered in solid, liquid or aerosol form, and whether it needs to be sterile for such routes of administration as injection. The compositions comprising one or more a polynucleotide of the present invention may be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 18th Ed. Mack Printing Company, 1990, incorporated herein by reference). A number of suitable formulations for use in the present invention are found in Remington's Pharmaceutical Sciences (Mack Publishing Company, Philadelphia, Pa., 17th ed., 1985) and in Dermatological Formulations: Percutaneous absorption, Barry (Ed.), Marcel Dekker Inc., 1983, both incorporated herein by reference. Moreover, for a brief review of methods for drug delivery, see Langer, Science 249:1527-1533, 1990, which is also incorporated herein by reference.

Preferably, the polynucleotides are fed or injected to stimulate an immune response. For example, the polynucleotides may be fed to the animal or injected into the animal prior to an infection or to improve an immune system purposely compromised by clinical treatment.

The composition can be any dose or effective amount of the composition that is safe and efficacious to achieve the desired result and may take into consideration the state of the individual's immune system. As the diseases, disorders or conditions that would benefit from these compositions are well known, the compositions may be designed such that they contain appropriate levels effective for treatment of the particular disease, disorder or condition. The compositions may generally be used in any formulation that is effective for treatment and the intended mode of administration.

The composition comprising the polynucleotide of the present invention can be delivered using any suitable method. In some cases, the polynucleotides are delivered by harmless bacteria retaining high levels of oligoribonucleotides <10 kDa grown as described in U.S. Pat. No. 7,678,551 or by the use of polymeric, biodegradable microparticle or microcapsule delivery devices known in the art. Another way to achieve uptake of the nucleic acid is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector comprising the polynucleotide of the present invention attached to poly-L-lysine by electrostatic or covalent forces. Poly-L-lysine binds to a ligand that can bind to a receptor on target cells (Cristiano, et al., 1995, J. Mol. Med. 73:479). Alternatively, tissue specific targeting can be achieved by the use of tissue-specific transcriptional regulatory elements that are known in the art. Delivery of "naked polynucleotides" (i.e., without a delivery vehicle) to an intramuscular, intradermal, or subcutaneous site is another means to achieve in vivo expression.

The polynucleotide of the present invention can be packaged with antibiotics for a convenient and well-recognized delivery system.

The polynucleotide of the present invention can be formulated into dosage forms for different administration routes utilizing conventional methods. For example, the polynucleotide of the present invention can be formulated in a capsule, a gel seal, or a tablet for oral administration. Capsules can contain any standard pharmaceutically acceptable materials such as gelatin or cellulose. Tablets can be formulated in accordance with conventional procedures by compressing mixtures of the polynucleotide of the present invention agent with a solid carrier and a lubricant. Examples of solid carriers include starch and sugar bentonite. The polynucleotide of the present invention can also be administered in a form of a hard shell tablet or a capsule containing a binder, e.g., lactose or mannitol, conventional filler, and a tableting agent. The polynucleotide of the present invention can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent.

The compositions of the invention can be administered to any part of the body that renders the composition safe and effective for treatment of a particular disease, disorder or condition. It will be appreciated that the present methods of treatment can be applied alone or in combination with treatments for these diseases, disorders or conditions. The compositions useful in the present methods can be administered one time or multiple times, depending on the composition, the severity of the disease, disorder, or condition, and the initial response of the condition to the treatment, for example, alleviating a symptom. For example, the compositions can be administered 1, 2, 4, or more times per day, and can be administered every 1, 2, 4, 7, or more days. Such treatments can be administered for a limited duration, or indefinitely until the condition or symptom has resolved. The compositions can be administered locally or systemically. In certain preferred embodiments of the invention the compositions comprise one or more polynucleotides of the present invention. For treatment of deep tissue, the polynucleotide of the present invention can be delivered directly to the tissues or surrounding tissues via injection.

In another aspect, the present invention provides pharmaceutically acceptable compositions which comprise a therapeutically-effective amount of one or more of the polynucleotides of the present invention described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam and (5) with antibiotics as a familiar delivery system.

VI. Utility

The polynucleotides of the present invention have the ability to stimulate neutrophils. The disclosed polynucleotides have utility as pharmaceuticals or consumables for treating or preventing a number of diseases, disorders or conditions associated with bacterial infections, an inadequate immune response in an animal to a microbial infection or pathogen, or a weakened immune system in general. Accordingly, the polynucleotides, compositions and methods of the present invention may be used to enhance or stimulate the immune response or system of an animal, e.g. to prevent an infection caused by a microorganism, ameliorate an infection caused by a microorganism, or kill an invading microorganism that causes infection. In particular, the polynucleotides, compositions and methods of the present invention may be used to treat or prevent bacterial infection in a mammal in need thereof. The polynucleotide of the present invention may be complementary to an Initiation Site of a bacterium that is different than the bacterium causing the infection in the animal or for which prevention is desired. The bacterium may belong to any phylum, class, order, family, genus or species. Exemplary genera include but are not limited to bacteria from *Mycobacteria, Chlamydia, Helicobacter, Lactobacillus, Staphylococcus, Streptococcus, Pediococcus, Pseudomonas,*

Bacillus, Escherichia, Listeria, Enterococcus, and Klebsiella, Acinetobacter, Borrelia, Yersinia, influenza viruses, West Nile virus, Bartonella, Ehrlichia, Rickettsia, Legionella, and Haemophilus. Exemplary species include Mycobacterium tuberculosis, Mycobacterium avium complex, Chlamydia pneumoniae, Helicobacter pylori, L. acidophilus, L. caseii, L. fermentum, L. plantarum, L. monocytogenes, L. innocua, S. aureus, S. typhimurium, P. acidolactici, B. coryneforme, E. coli, E. faecium, S. pyogenes, and K. pneumonia, B. henselae, R. typhi, B. burgdorferi, H. influenzae, L. pneumophila, E. chaffeenis, R. parkeri. In some cases, the bacterium, the fungus and the virus are resistant to antibiotics or other drugs.

Bacterial infections can cause or contribute to a variety of diseases, disorders or conditions including various forms of endocarditis, osteomyelitis, meningitis, skin and skin structure infections, pneumonias, bacteremias, intra-abdominal infections, genitourinary tract infections, abscesses, and necrotizing infections. Accordingly provided herein are methods, polynucleotides and compositions to treat or prevent such infections. Also included within the present invention are responses to other types of infections caused by other microorganisms, such as viruses, fungi and the like.

This invention can be better understood by reference to the following non-limiting examples. It will be appreciated by those skilled in the art that other embodiments of the invention may be practiced without departing from the spirit and the scope of the invention as herein disclosed and claimed.

EXAMPLES

Example 1

Neutrophil function is valuable for the assessment of the health status of animals. They are among the cells that represent the host's first line of cell defense. Phagocytic sentry cells, like dendritic cells, neutrophils and macrophages can be imbedded in tissues or move among the spaces in tissues. Being abundant in blood, neutrophils can quickly invade tissues inflamed by the presence of infection.

Neutrophils belong to a family of immune sentry cells responsible for host defense against many bacterial, viral and fungal infections. Circulating neutrophils respond to the site of inflammation raised by infected tissues. The interstitial spaces are opened, allowing the neutrophils to reach the infection site where they can engulf the microbe, hold it in a vacuole and bombard it with reactive oxygen intermediates, such as superoxides, hydrogen peroxide and hydroxyl radicals. Anti-microbial proteins and bactericidal enzymes like myeloperoxidase are also employed.

Killing microbes by the action of myeloperoxidase requires oxygen. Therefore, measuring the transient increase in oxygen uptake—the respiratory burst—by neutrophils reflects their antimicrobial activity. The respiratory burst, therefore, can be used as an indicator of the extent of neutrophil stimulation.

Exposing neutrophils isolated from the kidneys of fathead minnows to individual Oligos A and B and their complementary dimer, AB demonstrated significant stimulation. Oligo A can dimerize with itself which may explain why it had less broad stimulating activity than die Oligo B. It was determined by spectrofluorometry in a flow cytometer which recorded the oxidation of the non-fluorescent dihydrorhodamine 123 (DHR123) to fluorescent rhodamine during exposure of neutrophils to the oligos. Results were compared to the degree of fluorescence of a known powerful neutrophil stimulator, phorbol myristic acetate (PMA).

The degree of stimulation by PMA at a concentration of 1 μg/is represented in the accompanying graph as 100%. As can be seen Oligo B at a level of only 0.03 μg/ml stimulated the neutrophil population at a level of 30% of that from exposure to PMA at 1 μg/ml. Furthermore PMA is known to be toxic but, even 30 μg/ml of Oligo B did not indicate neutrophil destruction.

Neutrophils exhibit a large burst of oxidative factors after exposure to very low levels of 5'UUA UCC ACA3', SEQ ID NO:29. Oligo A is: 5'AAUAggUgU3', SEQ ID NO:27 and Oligo B is 5'UUAUCCACA3', SEQ ID NO:29.

Neutrophils from fathead minnows were prepared and tested by the Institute for International Cooperation in Animal Biologics, Iowa State Univ., Ames, Iowa 50011 (See: Immunomodulatory Effects of B-glucan on Neutrophil Function in Fathead Minnows, *Pimephales promelas Rafinesque*, 1820, Dev. and Comp. Immunol. (2006 30; 817-830), Palić, D., et al). Oligos were prepared by Oligos, Etc., Portland, Oreg. 97298).

| Oligo Conc. μg/ml | Oligo A % of PMA | Oligo B % of PMA | Oligo AB % of PMA |
| --- | --- | --- | --- |
| 30 | 16.21 | 14.93 | 31.45* |
| 3 | 0 | 33.02* | 0 |
| 0.3 | 0 | 18.32* | 0 |
| 0.03 | 11.83 | 29.57* | 23.23 |

Oligo B stimulated oxygen burst significantly higher than Oligo A at all tested concentrations. Oligo B stimulated oxidative burst significantly higher than mixtures of Oligos A and B at most concentrations ($P<0.05$ denoted by *).

The 9-membered consensus DNA core sequence found in most of the initiation sites of microbes is 5'AAUAGGTGT3' and, the consensus core ribonucleotide sequence is therefore 5'UUAUCCACA3'. Ribonucleotides containing up to 15 nucleotides in length are released during the first hour after bacteria enter pH neutral physiologic conditions. Those released later can interfere with the stimulatory activity of the ones released first. Mutations of, and around, the core consensus sequence have occurred although their successful execution is limited by the triple requirements of being necessarily complementary to the DNA sequence as well as the amino acid sequence in dnaA. Very high levels may desensitize the immune response, thereby protecting the animal from septic shock.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The therapeutic action observed by William Coley in treating cancerous tumors can be explained by the release of these oligoribonucleotides by the pathogens which he injected at the base of tumors. *S. pyogenes* releases such nucleotides.

What is claimed is:

1. A method of treating an animal to enhance, restore or stimulate its immune response comprising:
    administering to an animal in need thereof a therapeutically effective amount of a polynucleotide wherein said nucleotide comprises:
    (a) a full length complement to one or more Initiation Sites in the Origins of Replication of bacteria, fungi and virions,
    (b) a nucleic acid sequence selected from:

```
5' UAUU 3', 5' CCACA3', 5' AAUA 3',

5' GGUGU 3', 5' UUAUA 3', 5' UUA 3',

5'AUAA 3', 5'UUAU 3', 5'AAA 3',
```

-continued

```
5' UUU 3', 5' AAUA 3', 5' UUAU 3',

5' AUAA 3', 5' UAUU 3', 5' AAUAU 3',

5' UUAUA 3', and 5'UGUG'3; or
```

(c) a nucleic acid sequence which has 90% or greater sequence similarity to (a), wherein the polynucleotide contacts a neutophil or neutrophils belonging to the animal's immune network, and wherein said polynucleotide enhances, restores or stimulates the immune response of said neutrophil or neutrophils.

2. The method of claim 1, wherein the polynucleotide is selected from:

| | |
|---|---|
| 5'AAUAGGUGU3', | SEQ ID NO: 11 |
| 5'UUAUCCACA3', | SEQ ID NO: 13 |
| 5'AAACCUAUU3', | SEQ ID NO: 15 |
| 5'UUUGGAUAA3', | SEQ ID NO: 17 |
| 5'CCAAUAUGUG3', | SEQ ID NO: 19 |
| 5'GGUUAUACCAC3', | SEQ ID NO: 21 |
| 5'ACACCUAUU3', | SEQ ID NO: 23 |
| 5'UGUGGAUAA3', | SEQ ID NO: 25 |
| 5'AAUAxGUGU3', and | SEQ ID NO: 27 |
| 5'UUAUxCACA3'. | SEQ ID NO: 29 |

3. The method of claim 1, wherein said enhancement, restoration, or stimulation of said animal's immune response comprises (a) increasing the oxidative burst of cells of the immune network by releasing superoxide, hydrogen peroxide and myeloperoxidase and (b) the release of cytokines, interleukins and growth factors resulting in an enhanced immune response.

4. The method of claim 3, wherein said enhancement, restoration, or stimulation, of said animal's immune response comprises increased rejection of an infectious microbial agent, and protection against lethality induced by septic shock.

5. The method of claim 3, wherein said enhancement, restoration, or stimulation, of said animal's immune response comprises halting the growth of cancer cells or reducing immune dysfunction.

6. The method of claim 1, wherein the animal is administered the polynucleotide to treat an antibiotic resistant bacterium.

7. The method of claim 1, wherein the polynucleotide is administered intravenously, intradermally, intraarterially, intraperitoneally, intralesionally, intracranially, intraarticular, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically or via inhalation.

8. The method of claim 1, the dose of the polynucleotide administered is between 0.1 and 280 µg per Kg.

9. The method of claim 1, wherein the polynucleotide is fed to said animal as part of a food supplement, either in a Direct Fed Microbial or a bacteria-free preparation.

10. The method of claim 1, wherein the polynucleotide is fed to said animal in a tablet or gel once or twice a week.

11. The method of claim 10, wherein the immune system of an animal is restored comprising: by contacting a neutrophil in an animal with a therapeutically effective amount of a polynucleotide complementary to a portion of an initiation Site of an Origin of Replication of a bacterium, fungus or virus, so that the immune system of the animal is stimulated.

12. The method of claim 1, wherein the enhancement, restoration or stimulation of the immune response comprises increased neutrophil function, comprising a transient increase in oxygen uptake (respiratory burst).

13. The method of claim 1, wherein the enhancement, restoration or stimulation of the immune response comprises increased neutrophil function, comprising release of oxidative factors.

14. The method of claim 13, wherein the oxidative factors comprise superoxide, hydrogen peroxide and myeloperoxidase.

15. The method of claim 1, wherein the neutrophil is contacted with the polynucleotide ex vivo, in vivo, or in vitro.

* * * * *

UNITED STATES PATENT AND TRADEMARK OFFICE
CERTIFICATE OF CORRECTION

PATENT NO.         : 8,759,309 B2
APPLICATION NO.    : 13/031863
DATED              : June 24, 2014
INVENTOR(S)        : William E. Marshall Page 1 of 2

It is certified that error appears in the above-identified patent and that said Letters Patent is hereby corrected as shown below:

In the Claims

Col. 27, Claim 1, Line 7:
DELETE after (a) ","

Col. 27, Claim 1, Line 8:
DELETE after contacts a "neutophil"
ADD after contacts a --neutrophil--

Col. 27, Claim 2, Lines 15-33:
DELETE:
    5'AAUAGGUGU3', SEQ ID NO:11
    5'UUAUCCACA3', SEQ ID NO:13
    5'AAACCUAUU3', SEQ ID NO:15
    5'UUUGGAUAA3', SEQ ID NO:17
    5'CCAAUAUGUG3', SEQ ID NO:19
    5'GGUUAUACCAC3', SEQ ID NO:21
    5'ACACCUAUU3', SEQ ID NO:23
    5'UGUGGAUAA3', SEQ ID NO:25
    5'AAUAxGUGU3', SEQ ID NO:27 and
" 5'UUAUxCACA3', SEQ ID NO:29         "

Signed and Sealed this
Thirtieth Day of September, 2014

Michelle K. Lee
*Deputy Director of the United States Patent and Trademark Office*

ADD:

5'AAUAGGUGU3' (SEQ ID NO:11),
    5'UUAUCCACA3' (SEQ ID NO:13),
    5'AAACCUAUU3' ( SEQ ID NO:15),
    5'UUUGGAUAA3' (SEQ ID NO:17),
    5'CCAAUAUGUG3' (SEQ ID NO:19),
    5'GGUUAUACCAC3' (SEQ ID NO:21),
    5'ACACCUAUU3' (SEQ ID NO:23),
    5'UGUGGAUAA3' (SEQ ID NO:25),
    5'AAUAxGUGU3' (SEQ ID NO:27), and
-- 5'UUAUxCACA3' (SEQ ID NO:29). --